United States Patent
Leibler et al.

(10) Patent No.: US 9,642,790 B2
(45) Date of Patent: May 9, 2017

(54) AQUEOUS DISPERSION OF POLYMER PARTICLES, FILM-FORMING COMPOSITION CONTAINING SAME AND USES THEREOF

(71) Applicants: Vivatech, Paris (FR); Centre National de la Recherche Scientifique—CNRS, Paris (FR); Ecole Superieure de Physique et Chimie Industrielles de la Ville de Paris, Paris (FR)

(72) Inventors: Ludwik Leibler, Paris (FR); Francois Tournilhac, Paris (FR); Aggeliki Triftaridou, Paris (FR); Eva-Maria Leuschner, Augsburg (DE); Stephane Auguste, Ruffey les Echirey (FR); Jean-Marc Pernot, Dijon (FR)

(73) Assignees: Vivatech, Paris (FR); Centre National de la Recherche Scientifique—CNRS, Paris (FR); Ecole Superieure de Physique et Chimie Industrielles de la Ville de Paris, Paris (FR)

( * ) Notice: Subject to any disclaimer, the term of this patent is extended or adjusted under 35 U.S.C. 154(b) by 32 days.

(21) Appl. No.: 14/405,897

(22) PCT Filed: Jun. 7, 2013

(86) PCT No.: PCT/FR2013/051325
§ 371 (c)(1),
(2) Date: Dec. 5, 2014

(87) PCT Pub. No.: WO2013/182828
PCT Pub. Date: Dec. 12, 2013

(65) Prior Publication Data
US 2015/0174042 A1    Jun. 25, 2015

(30) Foreign Application Priority Data
Jun. 8, 2012   (FR) .................................... 12 55393

(51) Int. Cl.
| | | |
|---|---|---|
| C08L 33/12 | (2006.01) |
| A61K 9/10 | (2006.01) |
| A61K 8/37 | (2006.01) |
| A61K 8/81 | (2006.01) |
| A61K 47/32 | (2006.01) |
| C08J 5/18 | (2006.01) |
| C08F 265/06 | (2006.01) |
| A61K 9/70 | (2006.01) |
| A61K 8/44 | (2006.01) |
| A61Q 17/04 | (2006.01) |
| A61K 8/02 | (2006.01) |
| C08L 33/08 | (2006.01) |
| C08L 101/12 | (2006.01) |

(52) U.S. Cl.
CPC .......... *A61K 8/8147* (2013.01); *A61K 8/0279* (2013.01); *A61K 8/37* (2013.01); *A61K 8/44* (2013.01); *A61K 8/8152* (2013.01); *A61K 9/10* (2013.01); *A61K 9/7015* (2013.01); *A61K 47/32* (2013.01); *A61Q 17/04* (2013.01); *C08F 265/06* (2013.01); *C08J 5/18* (2013.01); *C08L 33/08* (2013.01); *C08L 33/12* (2013.01); *C08L 101/12* (2013.01); *A61K 2800/413* (2013.01); *A61K 2800/56* (2013.01); *C08J 2300/12* (2013.01); *C08J 2400/12* (2013.01); *C08L 2207/02* (2013.01)

(58) Field of Classification Search
CPC .................................. C08L 33/12; C08L 33/08
See application file for complete search history.

(56) References Cited

U.S. PATENT DOCUMENTS

| | | | | |
|---|---|---|---|---|
| 5,362,807 A * | 11/1994 | Nogura | .................. | C08F 265/06 525/282 |
| 6,531,185 B1 * | 3/2003 | Drujon | .................. | C08F 257/02 427/393.5 |
| 6,680,111 B1 * | 1/2004 | Leibler | ............. | B32B 17/10018 428/327 |

FOREIGN PATENT DOCUMENTS

| | | |
|---|---|---|
| EP | 0398489 | 11/1990 |
| JP | 2002138394 | 5/2002 |
| WO | 94/04581 | 3/1994 |
| WO | 2009/016053 | 2/2009 |
| WO | 2012/006402 | 1/2012 |

OTHER PUBLICATIONS

Kobayashi, H. et al. "Copolymer emulsion for coating moisture-proof paper," May 14, 2002, English translation of JP 2002-138394.*
Ye et al. ("Durable antibacterial finish on cotton fabric by using chitosan-based polymeric core-shell particles", J of Applied Polymer Science, Oct. 15, 2006).*
International Search Report in PCT/FR2013/051325 dated Sep. 24, 2013.

* cited by examiner

*Primary Examiner* — Gina Justice
(74) *Attorney, Agent, or Firm* — McAndrews, Held and Malloy

(57) ABSTRACT

The present invention concerns an aqueous dispersion of multiphase polymer particles in which the polymer particles comprise at least two separate phases, the internal phase being formed by polymerization in the presence of a cross-linking agent, said dispersion further comprising a surfactant chosen from amino acid derivatives. The invention also concerns a film-forming composition comprising said aqueous dispersion of polymer particles. The invention also relates to a film obtained after application of said film-forming composition. This film dries very quickly, is water resistant, and has good adhesion, elasticity and breaking strength properties. The invention also concerns the use of said film for protecting surfaces of the skin or mucous membranes, wounds, injuries and/or skin disorders.

19 Claims, No Drawings

AQUEOUS DISPERSION OF POLYMER PARTICLES, FILM-FORMING COMPOSITION CONTAINING SAME AND USES THEREOF

The present application is filed pursuant to 35 U.S.C. 371 as a U.S. National Phase application of International Patent Application No. PCT/FR2013/051325, which was filed Jun. 7, 2013, claiming the benefit of priority to French Patent Application No. 1255393, which was filed on Jun. 8, 2012. The entire text of the aforementioned applications is incorporated herein by reference in its entirety.

The invention relates to an aqueous dispersion of multiphase polymer particles and to its use in film-forming compositions which can, for example, be applied to the skin, mucous membranes, wounds, lesions and/or skin conditions. Another subject matter of the invention is the use of said dispersions to form physiologically acceptable films that may be applied to the skin.

PRIOR ART

Physiologically acceptable formulations comprising film-forming compositions of latex type (aqueous dispersions of polymers) are well known to one skilled in the art.

In patent application US 2010/0021409, Procter & Gamble describes, for example, a composition intended to be used as shaving foam. Said composition comprises one or more film-forming materials dispersed in an aqueous phase by surfactants. The film-forming materials can be polymers, such as polyvinylpyrrolidone or hydroxyethylcellulose, or copolymers, such as a styrene-acrylate or styrene-butadiene latex. Several surfactants are described, such as, in particular, sarcosinic acid derivatives and more particularly sodium N-myristoylsarcosinate. The compositions according to this document are shaving foams and do not in particular make it possible to form an isolable film which is elastic, is resistant to water, exhibits a good breaking strength and provides lasting protection of surfaces, such as, for example, the skin.

Latexes can in particular be used to form isolable films. In U.S. Pat. No. 5,173,291, for example, 3M describes a composition of latex type comprising an aqueous dispersion of copolymer comprising:

a "soft" monomer, the corresponding homopolymer of which has a Tg of less than −15° C., such as butyl acrylate, a "hard" monomer, the corresponding homopolymer of which has a Tg of greater than −5° C., such as methyl methacrylate, and a monomer capable of complexing iodine, such as N-vinylpyrrolidinone; said composition also comprising iodine for its antimicrobial properties and in order to stabilize the aqueous dispersion and also a surfactant in order to help in dispersing the latex particles in the aqueous phase.

This film-forming composition is intended to form a protective film on the skin, such as, in particular, a dressing.

However, the films formed by means of these compositions exhibit limited mechanical properties, in particular in terms of elasticity and of breaking strength.

There thus exists a need for novel film-forming compositions capable of easily and rapidly forming isolable films which are resistant to breaking, which are adherent, which exhibit good elasticity properties and which are resistant to water.

The Applicant has surprisingly found that it is possible to prepare films which dry rapidly and which exhibit excellent properties of adhesion, of elasticity and of resistance to water and to breaking by means of an aqueous dispersion of multiphase polymer particles in which the polymer particles comprise at least two distinct phases having different Tg values, the internal phase being formed by polymerization in the presence of a crosslinking agent, said dispersion comprising a surfactant chosen from amino acid derivatives. The film formed from this dispersion comprises at least two different Tg values.

A subject matter of the invention is thus, according to a first aspect of the invention, an aqueous dispersion of multiphase polymer particles in which the polymer particles comprise at least two distinct phases:

a first phase formed by a polymer $P_1$ of soft nature having a glass transition temperature ($Tg_1$) of less than 20° C., a second phase formed by a polymer $P_2$ of a hard nature having a glass transition temperature ($Tg_2$) of greater than 60° C., said dispersion comprising a surfactant chosen from amino acid derivatives and in which polymer $P_1$ is formed by polymerization in the presence of a crosslinking agent.

According to a second aspect, another subject matter of the invention is a film-forming composition comprising, in a physiologically acceptable medium, an aqueous dispersion of multiphase polymer particles.

The invention also relates, according to a $3^{rd}$ aspect, to a film exhibiting at least two different Tg values, said film comprising multiphase polymer particles and a surfactant, in which the polymer particles comprise at least two distinct phases:

a first phase formed by a polymer $P_1$ of soft nature having a glass transition temperature ($Tg_1$) of less than 20° C., a second phase formed by a polymer $P_2$ of hard nature having a glass transition temperature ($Tg_2$) of greater than 60° C., in which said surfactant is chosen from amino acid derivatives and in which polymer $P_1$ is formed by polymerization in the presence of a crosslinking agent.

Finally, a subject matter of the invention is, according to a fourth aspect, the use of the film described above for protecting surfaces of the skin, mucous membranes, wounds, lesions and/or skin conditions.

Aqueous Dispersion

A subject matter of the present invention is an aqueous dispersion of multiphase polymer particles.

Aqueous dispersions are understood to mean, within the meaning of the present patent application, a suspension of solid particles in a liquid phase comprising at least water.

The aqueous phase also comprises at least one surfactant chosen from amino acid derivatives, and optionally an oxidization/reduction system and/or a pH regulator and/or one or more pharmaceutical or cosmetic agents and/or one or more physiologically acceptable additives.

In particular, the aqueous phase can be present in the dispersion of the invention in a content ranging from 20% to 75% by weight, preferably from 40% to 70% by weight, based on the weight of the aqueous dispersion.

Multiphase Polymer Particles

Within the meaning of the present invention, the multiphase polymer particles are solid polymer particles which are dispersed in the aqueous phase.

Polymer is understood to mean, within the meaning of the present invention, a homopolymer or copolymer.

Said multiphase particles comprise at least two phases, each phase being composed of a polymer having very distinct properties, such as in particular different glass transition temperatures (Tg) for each phase.

Within the meaning of the present invention, glass transition temperature (Tg) of each phase of multiphase polymer particles is understood to mean either the Tg of the homopolymer as referenced in the literature or the Tg of the copolymer calculated by the Fox-Flory rule of mixtures. Indeed, the Tg of each phase cannot be directly measured on the multiphase particles as such.

When a phase of the particle is composed of a copolymer, a person skilled in the art can easily calculate the Tg of this phase by using in particular the Fox-Flory rule of mixtures. Thus, if one phase of the multiphase particle is composed of a copolymer which exhibits a mass fraction X a monomer A having a glass transition temperature Tg(A) and a mass fraction Y of a monomer B having a glass transition temperature Tg(B), then the glass transition temperature of the copolymer Tg(AB) can be estimated by applying the following relationship, the temperatures being expressed in kelvins:

$$\frac{1}{Tg(AB)} = \frac{X}{Tg(A)} + \frac{Y}{Tg(B)}$$

According to one embodiment, the first phase formed by polymer $P_1$ of soft nature can be the internal phase of the particle (also known as core) and the second phase formed by polymer $P_2$ of hard nature can be the external phase of the particle (also known as shell).

In particular, in the context of the invention, the polymer particles can be at least two-phase and exhibit a core/shell structure.

The soft nature of polymer $P_1$ can be reinforced by choosing a polymer $P_1$ having a $Tg_1$ of less than 20° C., preferably of less than 5° C. and more preferably still of less than 0° C.

For its part, the hard nature of polymer $P_2$ can be reinforced by choosing a polymer $P_2$ having a $Tg_2$ of greater than 60° C., preferably of greater than 70° C. and more preferably still of greater than 80° C.

According to a specific embodiment, polymer $P_1$ represents from 60% to 90% by weight of the particles and polymer $P_2$ represents from 10% to 40% by weight of the particles.

The first phase of the polymer particles according to the invention is obtained by polymerization of one or more monomers and of at least one crosslinking agent. The second phase of the polymer particles according to the invention can be obtained by polymerization of one or more monomers and optionally of one or more crosslinking agents.

The presence of a crosslinking agent in the first phase can in particular be used to structure said particle by crosslinking and in particular the first phase of said particle, which makes it possible to obtain a composition capable of forming a film that exhibits two glass transition temperatures in a controlled and reproducible manner.

According to a specific embodiment, polymer $P_1$ can comprise from 0.5% to 10% by weight, preferably from 1% to 7% by weight and more preferably from 2% to 5% by weight of units obtained by polymerization of a crosslinking agent, preferably chosen from group (II).

According to a specific embodiment, polymer $P_1$ can comprise:

from 90% to 99.5% by weight, preferably from 93% to 99% by weight and more preferably from 95% to 98% by weight of units obtained by polymerization of at least one monomer chosen from group (I); and from 0.5% to 10% by weight, preferably from 1% to 7% by weight and more preferably from 2% to 5% by weight of units obtained by polymerization of a crosslinking agent, preferably chosen from group (II).

According to another specific embodiment, polymer $P_2$ can comprise from 95% to 99.5% by weight, preferably from 97% to 99% by weight and more preferably 100% by weight of units obtained by polymerization of at least one monomer chosen from group (I).

When the second phase of the polymer particles is crosslinked, polymer $P_2$ can comprise from 0.5% to 5% by weight, preferably from 1% to 3% by weight, of units obtained by polymerization of a crosslinking agent, preferably chosen from group (II).

Within the meaning of the present patent application, the monomers of the group (I) can be chosen from: ($C_1$-$C_{16}$) alkyl esters of (meth)acrylic acid, such as methyl(meth) acrylate, ethyl(meth)acrylate and butyl(meth)acrylate, hydroxyalkyl esters of (meth)acrylic acid, vinyl esters of linear or branched carboxylic acids, such as vinyl acetate and vinyl stearate, styrene, alkylstyrenes, such as methylstyrene, haloalkylstyrenes, such as chloromethylstyrene, (meth)acrylamide, acrylonitrile, vinyl chloride, (meth) acrylic acids and their derivatives, such as anhydrides, monomers comprising acidic or basic functional groups, such as itaconic acid, fumaric acid, crotonic acid or maleic acid, silanated (meth)acrylic or vinyl monomers, such as methacryloyloxypropyltriethoxysilane or methacryloyloxypropyltriisopropoxysilane, monomers comprising acetoacetoxy groups, such as acetoacetoxyethyl(meth)acrylate, and mixtures thereof.

The crosslinking agents of group (II), within the meaning of the present patent application, can be chosen from the following monomers: allyl or ($C_1$-$C_{16}$)alkyl esters of monocarboxylic or dicarboxylic acids, such as allyl acrylate, allyl methacrylate, diallyl maleate or phthalate and dimethyl maleate, conjugated dienes, such as butadiene and isoprene, polyol poly(meth)acrylates, such as ethylene glycol dimethacrylate or triethylene glycol dimethacrylate, 1,3- or 1,4-butylene glycol dimethacrylate, 1,4-butanediol diacrylate and pentaerythritol tetraacrylate, trimethylolpropane triacrylate, polyvinylbenzenes, such as divinylbenzene or trivinylbenzene, and polyallyl derivatives, such as triallyl cyanurate, triallyl isocyanurate and triallyl trimesate, and mixtures thereof.

According to a preferred embodiment, the monomers of group (I) of polymer $P_1$ are chosen from butyl acrylate, methyl methacrylate and mixtures thereof.

According to another preferred embodiment, the crosslinking agents of group (II) of polymer $P_1$ are chosen from diallyl maleate, dimethyl maleate, 1,4-butanediol diacrylate and mixtures thereof.

According to another preferred embodiment, the monomer of group (I) of polymer $P_2$ is methyl methacrylate.

According to a preferred embodiment, polymer $P_2$ of the aqueous dispersion according to the invention can comprise at least 91% by weight, preferably at least 95% by weight and more preferably still 100% by weight of units obtained by polymerization of hydrophobic monomers. Indeed, such contents of hydrophobic monomers can make it possible, during the formation of the corresponding film, to obtain a hard, nontacky and water-resistant film. These properties are, on the contrary, detrimentally affected when the external layer of the particles comprises more than 10% of hydrophilic monomers.

Generally, the hydrophobic nature of a monomer is defined by its insolubility in water or its absence of affinity with respect to water. When a polymer is composed of hydrophobic monomers, said polymer is also regarded as hydrophobic. Within the meaning of the present patent application the hydrophobic nature of a polymer can be defined using the solubility parameter δ described in "Properties of Polymers" by D. W. Van Krevelen, 1990, 3rd edition, page 200. This parameter makes it possible to categorize the various polymers according to their affinity with respect to water. According to the invention, a polymer is hydrophobic if its δ is less than 26.

According to a preferred embodiment, the second phase of the polymer particles of the present invention does not comprise units obtained by polymerization of monomers comprising an acid functional group.

According to a specific embodiment, the polymer particles according to the invention comprise an intermediate phase, formed by a polymer $P_i$, between the first phase and the second phase. Advantageously, polymer $P_i$ of the intermediate phase exhibits a glass transition temperature $Tg_i$ of between 20 and 60° C. Polymer $P_i$ can in particular be formed by polymerization in the presence of a crosslinking agent. Polymer $P_i$ can comprise from 90% to 99.5% by weight, preferably from 93% to 99% by weight and more preferably from 95% to 98% by weight of units obtained by polymerization of at least one monomer chosen from group (I). Furthermore, polymer $P_i$ can comprise from 0.5% to 10% by weight, preferably from 1% to 7% by weight and more preferably from 2% to 5% by weight of units obtained by polymerization of a crosslinking agent chosen from group (II). Preferably, the monomers of group (I) of polymer $P_i$ are chosen from butyl acrylate, methyl methacrylate and mixtures thereof. Preferably, the crosslinking agents of group (II) of polymer $P_i$ are chosen from diallyl maleate, dimethyl maleate, 1,4-butanediol diacrylate and mixtures thereof.

According to a specific embodiment, the multiphase polymer particles are substantially spherical and exhibit a size of between 15 and 300 nanometers, preferably between 30 and 100 nanometers.

The multiphase polymer particles can in particular be present in the aqueous dispersion according to the invention in a content of between 25% and 70% by weight, preferably between 30% and 70% by weight, based on the weight of the aqueous dispersion.

Surfactant

The aqueous dispersion of multiphase particles according to the invention additionally comprises at least one surfactant. The surfactant may in particular be used to stabilize the suspension of multiphase polymer particles in the aqueous phase.

The surfactant used in the dispersion according to the invention is an amino acid derivative, such as, in particular, a derivative of sarcosinic acid or of glutamic acid.

The surfactant derived from amino acid can in particular be chosen from: sodium N-lauroylglutamate, disodium N-cocoylglutamate, sodium N-cocoylglutamate, sodium N-lauroylsarcosinate, sodium N-myristoylsarcosinate, sodium N-cocoylsarcosinate, sodium N-oleoylsarcosinate, ammonium N-lauroylsarcosinate and mixtures thereof.

According to a preferred embodiment, the surfactant is chosen from sodium N-lauroylsarcosinate, sodium N-myristoylsarcosinate and sodium N-lauroylglutamate, preferably sodium N-lauroylsarcosinate.

The choice of a surfactant derived from amino acids in the aqueous dispersions according to the invention makes it possible to prepare the preparation of aqueous polymer dispersions which are able to form films exhibiting improved mechanical properties and in particular a better elasticity, a better breaking strength and a better strain at break.

In addition to improving the mechanical properties of the film, the surfactants derived from amino acids exhibit a very low toxicity toward the environment (these surfactants are biodegradable) but also toward human beings. This low toxicity is thus an asset for the applications of the film according to the invention on the skin, wounds and/or mucous membranes. Mention may also be made, among the other noninsignificant advantages of these surfactants, of their compatibility with the pH of the skin and their low irritant potential.

Furthermore, the Applicant has surprisingly found that it is possible to further optimize the properties of the film obtained after application of the film-forming composition by adjusting the concentration and the nature of the surfactant. Indeed, when the concentration of surfactant is too low, the film can lose elasticity and become brittle. Conversely, when the concentration of surfactant is too high, the film can have a tendency to opacify and become white. Specifically, it has been found that, when the monomer to surfactant molar ratio is of the order of 30 or less than 30, the film obtained has a tendency to become white and, when this ratio is of the order of 190 or greater than 190, the film obtained has a tendency to crack.

Thus, the concentration of the surfactant in the aqueous dispersion according to the invention is preferably between 0.1% and 5% by weight, based on the weight of dry matter of the aqueous dispersion, preferably between 0.4% and 5% by weight and more preferably still between 0.7% and 2% by weight.

Oxidation/Reduction System

The aqueous phase of the dispersion according to the invention can optionally comprise an oxidation/reduction system which is able to promote initiation of the polymerization.

In the context of the invention, the oxidation/reduction system can be chosen from tert-butyl hydroperoxide/sodium bisulfite, to which sodium formaldehydesulfoxylate is optionally added, potassium persulfate/sodium bisulfite, to which sodium formaldehydesulfoxylate is optionally added, ammonium persulfate/sodium bisulfite, to which sodium formaldehydesulfoxylate is optionally added, potassium persulfate/sodium hydroxymethanesulfinate, and mixtures thereof.

The preferred oxidation/reduction system is potassium persulfate/sodium bisulfite and sodium formaldehydesulfoxylate.

The concentration of the oxidizing agent and of the reducing agent in the aqueous dispersion according to the invention can be between 0.01% and 5% by weight, preferably between 0.1% and 2% by weight, based on the weight of dry matter of the aqueous dispersion.

pH Regulator

The aqueous phase of the dispersion according to the invention can also comprise a pH regulator which can in particular be used to adjust the pH so as to optimize the polymerization. The pH regulators used in the present invention are those commonly used by a person skilled in the art. Such regulators are described in the following works: CRC Handbook of Chemistry and Physics, 76$^{th}$ ed. (pages 8-42), Bower, V. E. and Bates, R. G. J. Res. Nat. Bur. Stand., 55, 197, 1955, and Bates R. G. and Bower V. E., Anal. Chem., 28, 1322, 1956.

Preferably, the pH regulator is obtained by mixing, in various proportions, 0.1M aqueous solutions of $KH_2PO_4$ (potassium dihydrogenphosphate) and of NaOH (sodium hydroxide), as described in the Handbook of Chemistry and Physics, 76th ed., Chapter 8, pp. 8-42.

According to a specific embodiment, for a regulator at pH 6.0, 50 ml of $KH_2PO_4$ (0.1M) and 5.6 ml of NaOH (0.1M) are mixed in a 100 ml flask and the volume is made up to 100 ml with deionized water. For a regulator at pH 7.0, 50 ml of $KH_2PO_4$ (0.1M) and 29.1 ml of NaOH (0.1M) are mixed in a 100 ml flask and the volume is made up to 100 ml with deionized water. For a regulator at pH 7.5, 50 ml of $KH_2PO_4$ (0.1M) and 40.9 ml of NaOH (0.1M) are mixed in a 100 ml flask and the volume is made up to 100 ml with deionized water.

The pH regulator can also be used to control the acid-base form of the surfactant. Indeed, the surfactants derived from amino acids can exist in two forms depending on the pH of the reaction medium:

the neutral form, when the pH is greater than the pKa of the surfactant, the basic form, where the acid functional group has become a sodium carboxylate, when the pH is less than the pKa of the surfactant.

For stability reasons, it is preferable for the surfactant to be in its basic form, which corresponds to a pH of the aqueous dispersion greater than one unit above the pKa of the surfactant used (pH>pKa+1).

Generally, the pKa of the surfactants derived from amino acids within the meaning of the present invention must be less than the pH of the final emulsion. The pKa values can in particular be between 2 and 7 and preferably between 3 and 5.

The concentration of the pH regulator in the aqueous dispersion can in particular be between 5 mmol/l and 100 mmol/l, preferably between 10 mmol/l and 15 mmol/l, the concentration being expressed in moles of pH regulator per liter of aqueous dispersion.

In the case where the surfactant precipitates at a pH in the vicinity of 5, a buffer solution having a pH of between 5.8 and 8.0 can, for example, be prepared from 50 ml of a potassium dihydrogenphosphate solution (0.1 molar)+x ml of NaOH (0.1 molar), where x is a value tabulated as a function of the desired pH.

Pharmaceutical or Cosmetic Agents

The aqueous dispersion according to the invention can comprise, in addition to the abovementioned components, one or more pharmaceutical or cosmetic agents (or active agents), such as, in particular, antibacterial agents, antiseptics, antivirals, antifungal agents, painkillers, anti-inflammatories, agents which promote healing, hydrating agents, depigmenting agents, keratolytic agents, restructuring agents, anesthetics and sunscreens.

In particular, the active agents which can be introduced into the composition according to the invention can be chosen from:

antibacterials, such as polymyxine B, penicillins (amoxicillin), clavulanic acid, tetracyclines, minocycline, chlortetracycline, aminoglycosides, amikacin, gentamycin, neomycin, silver and its salts (silver sulfadiazine), or probiotics;

antiseptics, such as thiomersal, eosin, chlorhexidine, phenylmercuric borate, aqueous hydrogen peroxide solution, Dakin's solution, triclosan, biguanide, hexamidine, thymol, Lugol's solution, iodinated povidone, merbromin, benzalkonium chloride, benzethonium chloride, ethanol or isopropanol;

antivirals, such as aciclovir, famciclovir, ritonavir;

antifungals, such as polyenes, nystatin, amphotericin B, natamycin, imidazoles (miconazole, ketoconazole, clotrimazole, econazole, bifonazole, butoconazole, fenticonazole, isoconazole, oxiconazole, sertaconazole, sulconazole, thiabendazole, tioconazole), triazoles (fluconazole, itraconazole, ravuconazole, posaconazole, voriconazole), allylamines, terbinafine, amorolfine, naftifine or butenafine;

flucytosine (antimetabolite), griseofulvin, caspofungin or micafungin;

painkillers, such as paracetamol, codeine, dextropropoxyphene, tramadol, morphine and its derivatives, or corticoids and derivatives;

anti-inflammatories, such as glucocorticoids, nonsteroidal anti-inflammatories, aspirin, ibuprofen, ketoprofen, flurbiprofen, diclofenac, aceclofenac, ketorolac, meloxicam, piroxicam, tenoxicam, naproxen, indomethacin, naproxcinod, nimesulide, celecoxib, etoricoxib, parecoxib, rofecoxib, valdecoxib, phenylbutazone, niflumic acid or mefenamic acid;

active agents which promote healing, such as retinol, vitamin A, vitamin E, N-acetylhydroxyproline, *Centella asiatica* extracts, papain, silicones, essential oils of thyme, of niaouli, of rosemary and of sage, hyaluronic acid, synthetic polysulfated oligosaccharides having from 1 to 4 monosaccharide units, such as the potassium salt of octasulfated sucrose, the silver salt of octasulfated sucrose or sucralfate, or allantoin;

hydrating agents, such as hyaluronic acid, urea, glycerol, fatty acids, aquaporin modulators, vegetable oils, chitosan, certain sugars, including sorbitol, butters and waxes;

depigmenting agents, such as kojic acid (Kojic Acid SL®—Quimasso (Sino Lion)), arbutin (Olevatin®—Quimasso (Sino Lion)), the mixture of sodium palmitoylproline and European water lily extract (Sepicalm®—Seppic), undecylenoylphenylalanine (Sepiwhite®—Seppic), the licorice extract obtained by fermentation of *Aspergillus* and ethoxydiglycol (Gatuline Whitening®—Gattefossé), octadecenedioic acid (ODA White®—Sederma), α-arbutin (Alpha-Arbutin®, SACI-CFPA (Pentapharm)), the aqueous extract of *Arctostaphylos uva-ursi* leaves (Melfade-J®—SACI-CFPA (Pentapharm)), the complex plant mixture Gigawhite® (SACI-CFPA (Alpaflor)), diacetylboldin (Lumiskin®—Sederma), the satsuma extract (Melaslow®—Sederma), the mixture of lemon extract enriched in citric acid and of cucumber extract (Uninontan®U-34—Unipex), the mixture of *Rumex occidentalis* extract and of vitamin C (Tyrostat® 11—Unipex), oligopeptides (Melanostatin 5®—Unipex), kojic dipalmitate (KAD-15®—Quimasso (Sino Lion)), the complex of natural origin Vegewhite® from LCW, wheat germ extracts (Clariskin® II—Silab) or ethylenediaminetriacetate (EDTA);

keratolytic agents, such as salicylic acid, zinc salicylate, ascorbic acid, α-hydroxylated acids (glycolic, lactic, malic, citric or tartaric acid), silver maple, sour cherry or tamarind extracts, urea, the topical retinoid Keratoline® (Sederma), the proteases obtained by fermentation of *Bacillus subtilis*, the product Linked-Papain® (SACI-CFPA) or papain (proteolytic enzyme resulting from the *papaya* fruit);

restructuring active agents (for example restructuring active agents for superficial body growths), such as silica derivatives, vitamin E, camomile, calcium, horsetail extract or silk lipester;

anesthetics, such as benzocaine, lidocaine, dibucaine, pramoxine hydrochloride, bupivacaine, mepivacaine, prilocaine or etidocaine;

sunscreens, such as chemical screening agents (oxybenzone, sulisobenzone, dioxybenzone, Tinosorb S®, avobenzone, 2-ethoxyethyl p-methoxycinnamate, Uvinul® A+, Mexoryl® XL, octyl methoxycinnamate or octinoxate, octyl salicylate or octisalate, octyl triazone or Uvinul® T 150, methyl salicylate, meradimate, enzacamene, MBBT or Tinosorb® M, octyl cyanophenylcinnamate or Parsol® 340, para-aminobenzoic acid, ensulizole, Parsol® SLX or polysiloxane-15 or benzylidene malonate polysiloxane, Parsol® MCX or ethylhexyl methoxycinnamate, triethanolamine salicylate or trolamine salicylate, Mexoryl® SX or terephthalylidene dicamphor sulfonic acid) and inorganic screening agents (zinc oxides, titanium dioxide or kaolin).

During the preparation of the aqueous dispersion according to the invention, it is possible to choose to incorporate the active agent in the internal phase or the external phase of the multiphase polymer particle or else to leave it free in solution. The phase in which it is desired to incorporate the active agent will be chosen as a function of the chemical properties of the active agent. It will also be possible to choose the phase in which the active agent is incorporated depending on whether or not it is desired for said agent to be released.

Thus, for example, in order to incorporate the active agent in one of the phases of the multiphase polymer particles, said agent may be introduced simultaneously with the monomers which form the polymer of this phase.

According to a specific embodiment, the active agent incorporated in the internal phase of the multiphase polymer particle is a sunscreen, such as Parsol® MCX. This sunscreen is hydrophobic and should preferably remain at the surface of the skin, i.e. not be released, in order to be able to exert its screening properties and protect the skin from UV-B rays. Parsol® MCX can be incorporated in the internal phase of the particle, for example, to provide good dispersion and also good persistence of the active agent on the skin, once the film has been applied thereto. Thus, if a dispersion of multiphase polymer particles comprising a sunscreen in their internal phase is applied to the skin, a film which is particularly water resistant and which effectively protects the skin from the sun is obtained. As such, repeated applications of sunblock cream may be avoided, while providing the user with optimum sun protection. Indeed, it has been shown that no release of sunscreen is observed when the films obtained are washed with water.

According to another specific embodiment, the active agent is free in solution in the aqueous dispersion of multiphase polymer particles or in the composition comprising said dispersion.

In the context of the incorporation of an active agent, such as, in particular, a sunscreen intended to protect a surface, such as the skin, it is preferable for said active agent to be incorporated in one of the phases of the polymer particles rather than for it to be free in solution. Indeed, the active agent is thus better dispersed within the film (more homogeneous dispersion) and thus adheres better to the skin, which provides the skin with excellent protection against the rays of the sun.

Physiologically Acceptable Additives

The aqueous dispersion according to the invention can comprise, in addition to the abovementioned components, one or more physiologically acceptable additives, such as, for example, fragrances, flavorings, dyes, pigments, matifying agents, rheology agents or preservatives.

In the same way as for the pharmaceutical or cosmetic active agents, it is possible to choose, as a function of the solubility of the additive and of the polymerization stage at which said additive is added, whether said additive will be incorporated in the internal or external phase of the multiphase polymer particles or whether it will remain free in solution in the aqueous dispersion according to the invention.

Method of Preparation of the Aqueous Dispersion

The aqueous dispersion according to the invention can especially be obtained by emulsion polymerization according to techniques well known to a person skilled in the art. During the emulsion polymerization, the surfactant enable the formation of monomer droplets (also known as micelles) within which the polymerization takes place.

In the context of the invention, it is possible to prepare, in a first stage, polymer $P_1$ of soft nature constituting, for example, the internal phase of the particles in the presence of a crosslinking agent, preferably chosen from group (II), and to subsequently proceed to the preparation of polymer $P_2$ of hard nature constituting the external phase of the particles.

When the polymer particle comprises an intermediate phase formed by a polymer Pi, it is possible to prepare, in a first stage, polymer $P_1$ constituting the internal phase of the particles in the presence of a crosslinking agent, to proceed, in a second stage, to the preparation of polymer $P_i$ constituting the intermediate phase of the particles and to finish with the preparation of polymer $P_2$ constituting the external phase of the particles.

For each stage, the polymerization reaction is preferably carried out under an inert atmosphere at a temperature of between 25 and 150° C., according to the nature of the oxidation/reduction system used.

According to a preferred embodiment, the monomers are added to the aqueous phase either in the pure form or in the form of a preemulsion with a portion of the water and at least one surfactant over a period of time of, for a preparation of approximately 100 grams of aqueous dispersion, between 10 minutes and 3 hours, preferably between 15 and 90 minutes.

Film-Forming Composition

Another subject matter of the invention is a film-forming composition comprising, in a physiologically acceptable medium, an aqueous dispersion of multiphase polymer particles according to the invention.

Physiologically acceptable medium is understood to mean, within the meaning of the present invention, a medium which is compatible with the skin, mucous membranes, wounds, lesions and/or skin conditions.

The physiologically acceptable medium can in particular comprise water.

According to a preferred embodiment, the physiologically acceptable medium does not comprise a solvent other than water.

The composition according to the invention can comprise, in addition to the aqueous dispersion of multiphase particles, one or more pharmaceutical or cosmetic agents (or active agents) as defined above.

The composition according to the invention can also comprise one or more physiologically acceptable additives as defined above.

According to a preferred embodiment, the film-forming composition according to the invention comprises only the aqueous dispersion of multiphase polymer particles described above.

According to another preferred embodiment, the film-forming composition according to the invention comprises:
from 80% to 99.9% of aqueous dispersion of multiphase polymer particles described above,
from 0.1% to 20% of one or more pharmaceutical agents and/or of one or more additives.

According to a preferred embodiment, the film-forming composition according to the invention is liquid, that is to say that it flows under its own weight.

The film-forming compositions according to the invention can, for example, be prepared by adding, with stirring, the various active agents and additives to a dispersion of multiphase polymer particles according to the invention or conversely, by adding a dispersion of multiphase polymer particles according to the invention to an aqueous base comprising the various active agents and additives.

As explained above, the active agents and/or the physiologically acceptable additives can be incorporated in the internal phase or the external phase of the multiphase polymer particle or else they can be free in solution in the composition according to the invention.

Film

Another subject matter of the invention is, according to another aspect of the invention, a film exhibiting at least two different Tg values, said film comprising multiphase polymer particles and a surfactant, said polymer particles comprising at least two distinct phases:
a first phase formed by a polymer $P_1$ of soft nature having a glass transition temperature ($Tg_1$) of less than 20° C.,
a second phase formed by a polymer $P_2$ of hard nature having a glass transition temperature ($Tg_2$) of greater than 60° C.,
in which said surfactant is chosen from amino acid derivatives and in which polymer $P_1$ is formed by polymerization in the presence of a crosslinking agent.

The film exhibits two distinct Tg values which can be measured experimentally and which are in particular of the same order of magnitude as the Tg values of each of the two phases of the polymer particles constituting said film. However, the introduction of certain pharmaceutical agents during the preparation of one of the phases of the particle can result in a modification to the Tg value of the phase into which the pharmaceutical agent is introduced. In this case, a difference may be observed between one of the Tg values of the film which is measured experimentally and that measured in the absence of said agent.

The glass transition temperature of the film is understood to mean, within the meaning of the present invention, the glass transition temperature of the film, un-preheated (or not annealed), measured by DMA (Dynamic Mechanical Analysis, also known as DMTA for Dynamic Mechanical Thermal Analysis) at 1 Hz according to the method described below.

Dynamic mechanical analysis (DMA) measurements are carried out, starting from rectangular samples with dimensions of 10 mm×25 mm cut out from the film, using a DMA 2980 analyzer (TA Instruments) in the in-tension geometry of films by applying a pretension of 0.01N and operating at 1 Hz. The Tg values are the temperatures at which the dissipation factor tan(delta) passes through a maximum. These values are measured at the first heating at 3° C./min on un-preheated films.

Un-preheated films (or not annealed films) is understood to mean, within the meaning of the present invention, a film which has not been heated above 40° C.

The film can in particular be obtained by application of the film-forming composition according to the invention directly to a surface, followed by the evaporation of the water.

Thus, the composition can in particular be applied in a single layer to said surface. Preferably, a layer of 10 to 300 μm of the film-forming composition is produced.

The composition can be applied by all the means known to a person skilled in the art, such as a spray, a pen, a spatula and, in particular, with a brush.

Unexpectedly, the Applicant has found that the film obtained with the aqueous dispersions according to the invention exhibits a particularly rapid drying time, generally of less than two minutes. This property is particularly suitable for the production of films in situ, for example on the skin.

The Applicant has also observed that shorter drying times can also be obtained when the amount of water in the aqueous dispersion is reduced.

The film also exhibits an excellent resistance to water.

According to a preferred embodiment, the film obtained after drying exhibits excellent mechanical properties, which are determined by the method described below:

Films with a thickness of approximately 0.7 mm are obtained by evaporating a column of film-forming composition according to the present invention, with a height of approximately 2 mm, in a Teflon mold. Dumbbells of DIN 53504S3A shape (working length 12 mm, width 2 mm) corresponding to the standard ISO 527-3 are obtained by punching the sheet with a thickness of approximately 0.7 mm using a hollow punch. The mechanical measurements are carried out at a drawing rate of 10 mm/min using an Instron tensile testing device equipped with a 500N force sensor.

The results obtained show that the films of the present invention can have a good strain at break which can be above 150%, and also an excellent breaking strength which can be up to 5 MPa. Furthermore, the films of the present invention exhibit elastic conditions with an elastic modulus of the order of 50 MPa and a broad plastic domain with a yield point of the order of 3 MPa.

Finally, the film exhibits a very good adhesion to the support on which it is formed without, however, exhibiting a tacky aspect to the touch. The film also exhibits a good resistance to frictions.

Use of the Film

According to another aspect of the invention, the film can be applied on a surface to be protected. Thus, another subject matter of the invention is the use of the film described above to protect surfaces of the skin, mucous membranes, wounds, lesions and/or skin conditions. The film according to the invention thus has applications in the fields of dermatology and cosmetics. It can also be envisaged to apply the film according to the invention to skin appendages.

The film according to the invention also has applications in the field of the coatings of all types of materials, such as, for example, leather, plastic, plaster, board or paper, or composite materials, such as concrete or wood.

According to a preferred embodiment, the film-forming composition described above can be applied to the surface that is to be protected. After approximately two minutes, once the water has been completely evaporated, the treated surface is covered with an elastic film. The present invention is illustrated in more detail in the nonlimiting examples described below.

EXAMPLES

The following abbreviations are used in the examples:
MMA: methyl methacrylate
BuA: n-butyl acrylate
BDA: 1,4-butanediol diacrylate
DAM: diallyl maleate
SB: sodium bisulfite KPS: potassium persulfate
SFS: sodium formaldehydesulfoxylate
APS: ammonium persulfate Preparation A:

0.49 g of $Na_2HPO_4$ is placed in a 250 ml container and demineralized water is added so as to obtain 150 g of aqueous solution.

Preparation B:

2.8% by weight aqueous solution of the initiator SB (sodium bisulfite).

Preparation C (Surfactant: Sodium N-Lauroylsarcosinate):

54.2 g of BuA (423 mmol), 23.2 g of MMA (232 mmol), 0.8 g of crosslinking agent BDA (4 mmol) and 17 g of a 10% by weight aqueous solution of sodium N-lauroylsarcosinate (Schill+Seilacher GmbH, Perlastan L30) are introduced into a flat-bottomed glass container (internal diameter 55 mm) equipped with a magnetic stirrer (length 50 mm). The medium is stirred at 600 rpm until emulsified, i.e. for at least 5 minutes.

Preparation D (Surfactant: Sodium Dodecyl Sulfate):

54.2 g of BuA (423 mmol), 23.2 g of MMA (232 mmol), 0.8 g of crosslinking agent BDA (4 mmol) and 17 g of a 10% by weight aqueous solution of sodium dodecyl sulfate (SDS, Aldrich) are introduced into a flat-bottomed glass container (internal diameter 55 mm) equipped with a magnetic stirrer (length 50 mm). The medium is stirred at 600 rpm until emulsified, i.e. for at least 5 minutes.

Preparation E (Sunscreen: Parsol® MCX):

54.2 g of BuA (423 mmol), 23.2 g of MMA (232 mmol), 0.8 g of crosslinking agent BDA (4 mmol), 3.96 g of ethylhexyl methoxycinnamate (Parsol® MCX) and 17 g of a 10% by weight aqueous solution of sodium N-lauroylsarcosinate (Schill+Seilacher GmbH, Perlastan L30) are introduced into a flat-bottomed glass container (internal diameter 55 mm) equipped with a magnetic stirrer (length 50 mm) and protected from the light by aluminum foil. The medium is stirred at 600 rpm until emulsified, i.e. for at least 5 minutes.

Preparation F:

1.36 g of BuA (10.61 mmol), 3.37 g of MMA (33.66 mmol), 0.3 g of crosslinking agent DAM (1.53 mmol) and 0.49 g of preparation B (i.e., 0.136 mmol of initiator SB) are introduced into a flat-bottomed glass container (internal diameter 30 mm) equipped with a magnetic stirrer (length 20 mm). The medium is stirred at 600 rpm until emulsified, i.e. for at least 5 minutes.

Preparation G:

11.71 g of MMA (117 mmol) and 3.82 g of water are introduced into a flat-bottomed glass container (internal diameter 30 mm) equipped with a magnetic stirrer (length 20 mm). The medium is stirred at 600 rpm until emulsified, i.e. for at least 5 minutes.

Preparation H (Sunscreen: Parsol® MCX):

11.71 g of MMA (117 mmol), 3.61 g of Parsol® MCX and 3.82 g of water are introduced into a flat-bottomed glass container (internal diameter 30 mm) equipped with a magnetic stirrer (length 20 mm) and protected from the light by aluminum foil. The medium is stirred at 600 rpm until emulsified, i.e. for at least 5 minutes.

Example 1: (Comparative) Preparation of an Aqueous Dispersion of Monophase Polymer Particles with a Surfactant Derived from Amino Acid 115 g of preparation A (i.e., 2.65 mmol of $Na_2HPO_4$) are introduced into a round-bottomed reactor with an internal diameter of 100 mm equipped with an anchor-shaped glass stirrer and degassed beforehand with nitrogen, followed by an introduction under nitrogen of preparation C.

The reaction temperature is adjusted to 70° C. using an external oil bath of adjustable height and the mixture is stirred at 260 rpm under nitrogen. 10 minutes after the end of the addition, 2.62 g of preparation B (i.e., in moles, 0.73 mmol of initiator) are introduced dropwise into the mixture at a fixed rate over five minutes. Then, after stirring for a further ten minutes, 0.34 g of KPS (1.25 mmol) in solution in 7.7 g of demineralized water are added to the mixture via a peristaltic pump over a period of time of 2 minutes. After one hour, the reaction mixture is cooled, still with stirring. The emulsion obtained (referred to as emulsion 1) is collected in a container as soon as the temperature is less than 35° C.

Example 2: Preparation of an Aqueous Dispersion of Multiphase Polymer Particles with a Surfactant Derived from Amino Acid According to the Invention 150 g of emulsion 1 are placed at 70° C., under nitrogen and with stirring as above, in the reactor described above. The preparation F is then added by means of a peristaltic pump over a period of time of 2 minutes. 0.015 g of KPS (0.055 mmol) dissolved in 0.7 g of demineralized water is then introduced by means of a peristaltic pump over a period of time of 10 minutes. Stirring is maintained at 70° C. for 60 minutes, then 2.20 g of a 1.74% by weight aqueous solution of SFS (i.e., 0.25 mmol of SFS) are added in one minute using a peristaltic pump and then, in parallel, using two peristaltic pumps, the preparation G and 10 g of a 0.5% by weight aqueous solution of ammonium persulfate (i.e., 0.22 mmol of APS) are added over a period of 15 minutes. After addition, the temperature of the reactor is maintained at 70° C. for 30 minutes. After this, the remaining reactive entities are deactivated by adding a mixture of 0.46 g of an aqueous ammonium persulfate solution (15.61% by weight) and 0.32 g of an aqueous SB solution (2.8% by weight). The reaction is thus maintained at 70° C. for 30 minutes. Stirring is then maintained but heating is halted by lowering the oil bath. The emulsion (referred to as emulsion 2) is collected as soon as the temperature is less than 35° C.

Example 3: (Comparative) Preparation of an Aqueous Dispersion of Multiphase Polymer Particles with the Surfactant Sodium Dodecyl Sulfate The procedure of example 1 is followed but using the preparation D instead of the preparation C. An emulsion 3 is obtained and is converted into emulsion 4 by following the procedure of example 2.

Example 4: Comparison of the Emulsions of Examples 1 to 3

Comparison of the Particle Sizes

Measurements by DLS (Dynamic Light Scattering) were carried out using an ALV/CGS3 goniometer equipped with an ALV/LSE 5004 multi-T correlator and with an He—Ne laser at a wavelength of 632.8 nm. The measurements were carried out on samples with a diameter of 10 mm over seven scattering angles ranging from 60° to 120° with an incrementation of 10°. The system was maintained at 23° C. Each sample was prepared as follows: 20 ml of Milli-Q® water, filtered twice through a syringe filter with a porosity of 0.22 µm, are placed in a glass flask. 5 µl of emulsion are injected therein using a micropipette. These samples are then analyzed in sequences of 100 seconds for each angle value; the data collected are then processed by cumulant analysis.

In emulsion 1, the particles are spherical and have a mean diameter of approximately 36-38 nm, measured by DLS.

Emulsion 2 has a pH of between 6 and 7 and the dry matter portion is approximately 40%. The dispersed polymer particles are spherical and have a mean diameter of approximately 38-42 nanometers, measured by DLS. The phase of soft nature of the particles, composed of a mixture of butyl acrylate and methyl methacrylate, represents approximately 80% of the total weight of the particles and the phase of hard nature, composed of methyl methacrylate, represents approximately 20% of the total weight of the particles.

In emulsion 4, the particles are spherical and have a mean diameter of approximately 47-49 nm, measured by DLS.

Comparison of the Mechanical Properties of the Thick Films Obtained with Emulsion 1 (Comparative), Emulsion 2 (According to the Invention) and Emulsion 4 (Comparative)

Films with a thickness of approximately 0.7 mm are obtained by evaporating a column of emulsion 2 with a height of approximately 2 mm in a Teflon mold. Dumbbells of DIN 53504S3A shape (working length 12 mm, width 2 mm) corresponding to the standard ISO 527-3 are obtained by punching the sheet with a thickness of approximately 0.7 mm using a hollow punch.

The mechanical measurements are carried out at a drawing rate of 10 mm/min using an Instron tensile testing device equipped with a 500N force sensor and gave the following results:

Dynamic mechanical analysis (DMA) measurements are carried out, starting from rectangular samples with dimensions of 10 mm×25 mm cut out from the same film, using a DMA 2980 analyzer (TA Instruments) in the in-tension geometry of films by applying a pretension of 0.01N and operating at 1 Hz. The Tg values are the temperatures at which the dissipation factor tan(delta) passes through a maximum.

These values are measured at the first heating at 3° C./min on films not preheated.

The films obtained with emulsion 1 exhibit the following characteristics:
Breaking stress: 0.25 MPa
$Tg_1$=−5° C.

The films obtained with emulsion 2 exhibit the following characteristics:
Elongational elastic modulus: 48 MPa
Yield point: 2.6 MPa
Breaking stress: 3.7 MPa
Nominal strain at break: 250%
The measurement of strain by video extensiometry showed that the strain at break is greater than 150%
$Tg_1$=−3° C., $Tg_2$=70° C.

The films obtained with emulsion 4 exhibit the following characteristics:
Breaking stress: 0.85 MPa The mechanical measurements carried out on the films obtained with emulsion 1 show that the films break for a lower stress, of the order of 0.25 MPa, than the films obtained with emulsion 2 according to the invention. Furthermore, for the films obtained with emulsion 1, plastic strain is observed even for low applied stresses.

This example shows that the films produced from monophase particles (emulsion 1) have inferior mechanical properties to those obtained from particles of multiphase structure according to the invention (emulsion 2).

The mechanical measurements carried out on the films obtained with emulsion 4 show that the films break for a lower stress, of the order of 0.85 MPa, than the films obtained with emulsion 2 according to the invention. Furthermore, for the films obtained with emulsion 4, plastic strain is observed even for low applied stresses.

This example also shows that the films produced from multiphase particles have superior mechanical properties when an amino acid derivative, such as sodium N-lauroyl-sarcosinate, is used as surfactant instead of SDS, as in the prior art.

Example 5: Incorporation of Active Agent after Polymerization (Free in Solution)

A sample of 8 g of emulsion 2 (example 2) is centrifuged at 14 000 rpm (r=0.08 m), i.e. a radial acceleration of 17 500 g, for 1 hour at 40° C. The pellet is retained and the supernatant is removed and replaced with 16.11 ml of ethanol and 9.7 microliters of a 0.07M solution of Parsol® MCX (ethylhexyl methoxycinnamate) in ethanol, i.e. an initial concentration of 43.3 micromol/liter. After standing for 24 hours sheltered from light, the emulsion is centrifuged again under the same conditions. The analysis of the supernatant by ultraviolet spectrometry gives, at 308 nm, an absorbance of 0.325. At the same wavelength, standard solutions of 2.78 micromol/liter and 4.48 micromol/liter of Parsol® MCX in ethanol have absorbances of 0.317 and 0.345 respectively.

Example 6: Incorporation of Active Agent in the Internal Phase of the Polymer Particles The procedure of example 1 is followed, except that preparation E is used instead of preparation C and that the reactor and the flasks are protected from light with aluminum foil. The resulting emulsion is subsequently converted according to the procedure of example 2 while protecting the reactor and the flasks from light with aluminum foil.

The size of the particles of the emulsion obtained, measured by light scattering (DLS), is approximately 36-38 nm.

Example 7: Incorporation of Active Agent in the External Phase of the Polymer Particles The procedure of example 2 is followed, except that preparation H is used instead of preparation G and that the reactor and the flasks are protected from light with aluminum foil.

The final size of the particles, measured by light scattering (DLS), is approximately 40-44 nm.

A film is produced from this emulsion under conditions identical to those of example 4 but sheltered from light.

The Tg values, measured in the same way as in example 4, are:
$Tg_1$=−8° C., $Tg_2$=55° C.

The mechanical properties, measured in the same way as in example 4, give the following results:
Elongational elastic modulus: 10 MPa
Yield point: 1 MPa
Breaking stress: 2.1 MPa
Nominal strain at break: 250%

Example 8: Comparative Measurement of the Transmittance of the Films Formed from the Emulsions of Examples 2 and 7

The transmittance of the film obtained in example 7 is measured in the visible region at 530 nm and in the UVB region at 308 nm using a Jasco V-530 spectrometer, the film being placed as close as possible to the detector. The same measurement is carried out on a control film devoid of sunscreen produced according to example 2.

The following results are obtained:

| Film | Transmittance at 308 nm | Transmittance at 530 nm |
|---|---|---|
| According to example 2 | 49% | 77% |
| According to example 7 | 0.07% | 80% |

Example 9: Application of the Film-Forming Composition According to the Invention The film-forming composition of example 2 is applied with a brush, in a single layer of 150 μm, to a clean and dry skin surface of 3 cm².

After two minutes, the water is completely evaporated and the skin is covered with a film which is elastic, which adheres to the skin for several hours, which is not tacky and which resists water, in particular several hand washing operations.

The invention claimed is:

1. An aqueous dispersion of multiphase polymer particles in which the polymer particles comprise at least two distinct phases:
    a first phase formed by a polymer $P_1$ of soft nature having a glass transition temperature ($Tg_1$) of less than 20° C.,
    a second phase formed by a polymer $P_2$ of hard nature having a glass transition temperature ($Tg_2$) of greater than 60° C.,
said dispersion comprising a surfactant chosen from amino acid derivatives and in which polymer $P_1$ is a crosslinked polymer formed by polymerization in the presence of a crosslinking agent, and wherein polymer $P_2$ comprises at least 95% by weight of until obtained by polymerization of hydrophobic monomers, and wherein the surfactant derived from amino acids is chosen from sarcosinic acid derivatives and glutamic acid derivatives.

2. The aqueous dispersion as claimed in claim 1, wherein the phase formed by polymer $P_1$ of soft nature is the internal phase of the particle and the phase formed by polymer $P_2$ of hard nature is the external phase of the particle.

3. The aqueous dispersion as claimed in claim 1, wherein the multiphase polymer particles are substantially spherical and exhibit a diameter of between 15 and 300 nanometers.

4. The aqueous dispersion as claimed in claim 1, wherein polymer $P_1$ represents from 60% to 90% by weight of the particles and polymer $P_2$ represents from 10% to 40% by weight of the particles.

5. The aqueous dispersion as claimed in claim 1, wherein polymer $P_1$ comprises:
    from 90% to 99.5% by weight of units obtained by polymerization of at least one monomer chosen from group (I) comprising ($C_1$-$C_{16}$)alkyl esters of (meth) acrylic acid, hydroxyalkyl esters of (meth)acrylic acid, vinyl esters of linear or branched carboxylic acids, styrene, alkylstyrenes, haloalkylstyrenes, (meth)acrylamide, acrylonitrile, vinyl chloride, (meth)acrylic acids and their derivatives, monomers comprising acidic or basic functional groups, silanated (meth)acrylic or vinyl monomers, monomers comprising acetoacetoxy groups, and mixtures thereof; and
    from 0.5% to 10% by weight of units obtained by polymerization of a crosslinking agent.

6. The aqueous dispersion as claimed in claim 5, wherein the crosslinking agent is chosen from group (II) comprising allyl or ($C_1$-$C_{16}$)alkyl esters of monocarboxylic or dicarboxylic acids, conjugated dienes, polyol poly(meth)acrylates, polyvinylbenzenes, polyallyl derivatives, and mixtures thereof.

7. The aqueous dispersion as claimed in claim 1, wherein polymer $P_2$ comprises from 95% to 99.5% by weight of units obtained by polymerization of at least one monomer chosen from group (I) as defined in claim 5.

8. The aqueous dispersion as claimed in claim 5, wherein the monomers of group (I) of polymer $P_1$ are chosen from butyl acrylate, methyl methacrylate and mixtures thereof.

9. The aqueous dispersion as claimed in claim 6, wherein the crosslinking agents of group (II) of polymer $P_1$ are chosen from diallyl maleate, dimethyl maleate, 1,4-butanediol diacrylate and mixtures thereof.

10. The aqueous dispersion as claimed in claim 7, wherein the monomer of group (I) of polymer $P_2$ is methyl methacrylate.

11. The aqueous dispersion as claimed in claim 1, wherein polymer $P_2$ comprises 100% by weight of units obtained by polymerization of hydrophobic monomers.

12. The aqueous dispersion as claimed in claim 1, wherein the surfactant derived from amino acids is chosen from sodium N-lauroylglutamate, disodium N-cocoylglutamate, sodium N-cocoylglutamate, sodium N-lauroylsarcosinate, sodium N-myristoylsarcosinate, sodium N-cocoylsarcosinate, sodium N-oleoylsarcosinate, ammonium N-lauroylsarcosinate and mixtures thereof.

13. The aqueous dispersion as claimed in claim 1, wherein the concentration of the surfactant is between 0.1% and 5% by weight, based on the weight of dry matter of the aqueous dispersion.

14. The aqueous dispersion as claimed in claim 1, wherein the pH of the aqueous dispersion is greater than one unit above the pKa of the surfactant used.

15. The aqueous dispersion as claimed in claim 1, wherein it comprises an active agent chosen from antibacterial agents, antiseptics, antivirals, antifungal agents, painkillers, anti-inflammatories, agents which promote healing, hydrating agents, depigmenting agents, keratolytic agents, restructuring agents, anesthetics and sunscreens.

16. The aqueous dispersion as claimed in claim 15, wherein the active agent is incorporated in an internal phase or in an external phase of the multiphase polymer particles.

17. A film-forming composition comprising, in a physiologically acceptable medium, an aqueous dispersion of multiphase polymer particles as claimed in claim 1.

18. The film-forming composition as claimed in claim 17, wherein it comprises a pharmaceutical agent chosen from antibacterial agents, antiseptics, antivirals, antifungal agents, painkillers, anti-inflammatories, agents which promote healing, hydrating agents, depigmenting agents, keratolytic agents, restructuring agents, anesthetics and sunscreens.

19. A process for protecting surfaces of the skin, mucous membranes, wounds, lesions and/or skin conditions comprising applying the film-forming composition as defined in claim 17 to the surface that is to be protected.

* * * * *